US012508441B2

(12) United States Patent
Li et al.

(10) Patent No.: US 12,508,441 B2
(45) Date of Patent: Dec. 30, 2025

(54) QUANTUM GRAPHENE GENERATOR

(71) Applicants: Zhi-Min Li, Taichung (TW); Ching-Cheng Tsai, Taichung (TW)

(72) Inventors: Zhi-Min Li, Taichung (TW); Ching-Cheng Tsai, Taichung (TW)

( * ) Notice: Subject to any disclaimer, the term of this patent is extended or adjusted under 35 U.S.C. 154(b) by 411 days.

(21) Appl. No.: 18/218,139

(22) Filed: Jul. 5, 2023

(65) Prior Publication Data

US 2025/0010098 A1 Jan. 9, 2025

(51) Int. Cl.
*A61N 5/06* (2006.01)

(52) U.S. Cl.
CPC .... *A61N 5/0624* (2013.01); *A61N 2005/0631* (2013.01); *A61N 2005/0632* (2013.01); *A61N 2005/066* (2013.01)

(58) Field of Classification Search
CPC .... A61N 2005/0631; A61N 2005/0632; H01F 7/064
See application file for complete search history.

(56) References Cited

U.S. PATENT DOCUMENTS 11,657,941 B2 5/2023 Tsai

FOREIGN PATENT DOCUMENTS

TW M615562 U * 8/2021
TW M641331 U 5/2023

OTHER PUBLICATIONS

English Translation of TW M641331 (Year: 2023).*
English Translation of TW M615562 (Year: 2021).*

* cited by examiner

*Primary Examiner* — Kaitlyn E Smith
(74) *Attorney, Agent, or Firm* — LANWAY IPR SERVICES; Chun-Ming Shih

(57) ABSTRACT

A quantum graphene generator contains: a far-infrared quantum implantation device which includes: a body, a lid, a crystal quartz, a plasma sheet, an intermediate-frequency current device, a magnet assembly, and an energy medium. The body includes an accommodation chamber. The lid is covered on the body and includes a receiving space. The crystal quartz is received in the accommodation chamber and includes the energy medium. The plasma sheet is comprised of multiple multi-stranded coil layers, multiple copper adhering layers, and a copper sheet. The intermediate-frequency current device includes multiple magnetic elements. A top of the magnet assembly is arranged on a middle copper adhering layer below the top copper adhering layer, and a bottom of the magnet assembly is located on the energy medium to increase the magnetic field. The energy medium includes a graphene defined therein, a top of the energy medium is arranged on the magnet assembly, and a bottom of the energy medium is arranged on the top of the crystal quartz.

5 Claims, 8 Drawing Sheets

QUANTUM GRAPHENE GENERATOR

TECHNICAL FIELD

The present disclosure relates to a quantum graphene generator which is applied to implant far-infrared quantum to energy media (graphene), thus releasing far-infrared quantum from the graphene.

BACKGROUND

Conventionally, graphene is a single-layer two-dimensional crystal composed of carbon atoms in sp2 mixed orbitals to form a hexagonal arrangement in a honeycomb crystal lattice. The structure of the graphene is quite stable, and this stable lattice structure makes graphene have excellent thermal conductivity. Scientists have discovered that graphene oxide is effective at inhibiting the growth of *Escherichia coli* without harming human cells. Graphene oxide is also antibacterial to other bacteria, and graphene-derived compounds are thought to have applications in cancer treatment. It is that graphene oxide can recognize the difference in electron density between cancer cells and normal cells, and then attach to cancer stem cells so that it can be acted on by targeted drugs and achieve the effect of inhibiting distant metastasis of tumors. This breakthrough discovery can make up for the shortcomings of traditional chemotherapy and radiotherapy that can only kill differentiated cancer cells, and is expected to achieve a higher treatment response rate and patient survival rate. At present, the team has experimentally proved that graphene oxide can inhibit the formation of tumor spheres in six cancers (breast cancer, pancreatic cancer, brain cancer, lung cancer, ovarian cancer, and prostate cancer), thus inhibiting their spread.

Far-infrared quantum are used as the energy absorbed by the organic polymer resonance, so it is easy to act on the reactant of the biochemical reaction and promote the reaction. After cells receive far-infrared quantum, they can increase resonance energy, promote cell activity (activate cells), further accelerate metabolism, help cell proliferation and synthesis of biochemical substances of various enzymes, catalyze biochemical reactions and improve the immune system operation. At the same time, after the cells receive the far-infrared quantum, the resistance of the cells to harmful substances (oxidative free radicals) will be improved and increase the antioxidant capacity of cells and the life cycle of cells. The far-infrared quantum will activate the cells and water in the human body, activate the activation, improve the solubility, penetration and transport efficiency of biochemical substances in water, and help the biochemical reactions to proceed. Accordingly, the far-infrared quantum is a great help for the health of the human body.

A conventional resonant energy stabilizer is disclosed in U.S. Pat. No. 11,657,941B2. The resonant energy stabilizer contains: a sapphire arranged in a center of a mineral crystal, a white crystal, a citrine and a green crystal which are surrounded around the sapphire, and a plurality of titanium crystals surrounded around the white crystal, the citrine and the green crystal. However, the sapphire, white crystal, citrine, green crystal and titanium crystal are too expensive to reduce the production cost.

A conventional quantum implanting device of graphene transparent edible raw material is disclosed in TW Utility Model No. M641331. The quantum implanting device contains a sapphire fixed on a center of crystal quartz. But such a sapphire costs high price, thus causing expensive fabrication cost.

The present invention has arisen to mitigate and/or obviate the afore-described disadvantages.

SUMMARY

A primary aspect of the present invention is to provide a quantum graphene generator which is capable of partially using some high-energy natural mineral crystals which are crystalline semi-precious stones with dozens of important trace elements of the earth, and combined with the patented plasma technology, step by step to create benefit to human health, thus producing a quantum graphene generator.

To obtain above-mentioned aspect, a quantum graphene generator provided by the present invention contains: a far-infrared quantum implantation device which includes: a body, a lid, a crystal quartz, a plasma sheet, an intermediate-frequency current device, a magnet assembly, and an energy medium.

The body includes an accommodation chamber defined therein and configured to receive the crystal quartz, the plasma sheet, the magnet assembly, and the energy medium.

The lid is covered on the body, and the lid includes a receiving space defined therein and configured to accommodate the intermediate-frequency current device.

The crystal quartz is received in the accommodation chamber of the body, and the crystal quartz includes the energy medium arranged on a top thereof.

The plasma sheet is a plasma sheet assembly which is in a quantum level, the plasma sheet is comprised of multiple multi-stranded coil layers, multiple copper adhering layers, and a copper sheet. The multiple multi-stranded coil layers are made of a copper bundle twisted from multiple copper wires, and the multiple multi-stranded coil layers are covered by an insulation layer. A respective one copper adhering layers is in a plate shape and is stacked with a respective one stranded coil layer and the respective one copper adhering layer, and the copper sheet is defined between the respective one stranded coil layer and the respective one copper adhering layer to produce radiated waves of a magnetic field.

The intermediate-frequency current device includes multiple magnetic elements which are adhered on a top copper adhering layer of the multiple copper adhering layers and are configured to increase the radiated waves of the magnetic field, and the intermediate-frequency current device inputs direct currents (DC) and increases a voltage of the DC to produce high-voltage microcurrent, the microcurrent produces the radiated waves of the magnetic field via the multiple magnetic elements and the multiple copper adhering layers, then the radiated waves of the magnetic field impact the crystal quartz to generate electric pulse wave.

A top of the magnet assembly is arranged on a middle copper adhering layer below the top copper adhering layer, and a bottom of the magnet assembly is located on the energy medium to increase the magnetic field.

The energy medium includes a graphene defined therein, a top of the energy medium is arranged on the magnet assembly, and a bottom of the energy medium is arranged on the top of the crystal quartz, such that far-infrared quantum is implanted to the graphene, thus releasing far-infrared quantum from the graphene.

Other objects and features will be in part apparent and in part pointed out hereinafter.

DETAILED DESCRIPTION

Figure 1:
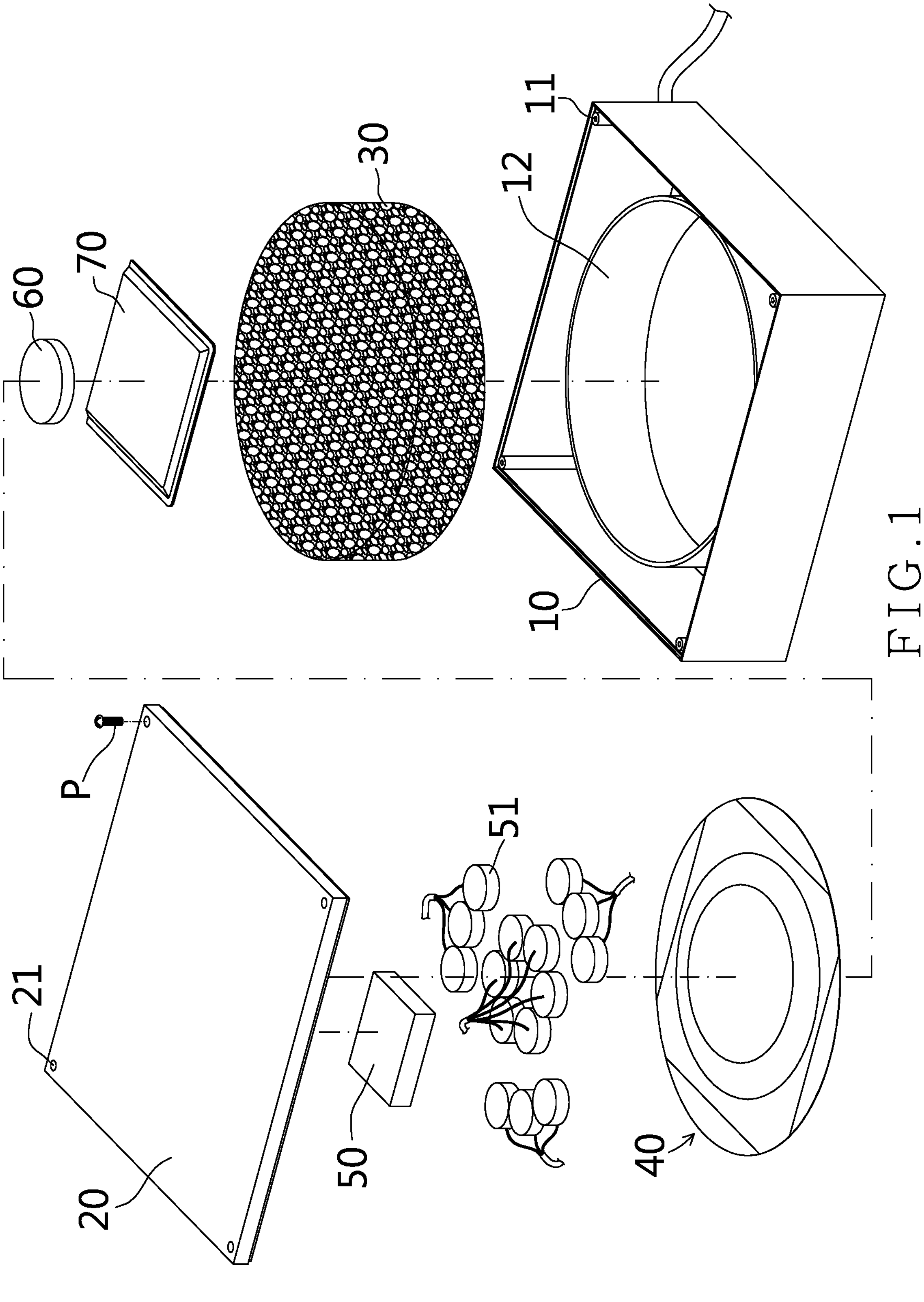
FIG. 1 is a perspective view showing the exploded components of a quantum graphene generator according to a preferred embodiment of the present invention.
Figure 2:
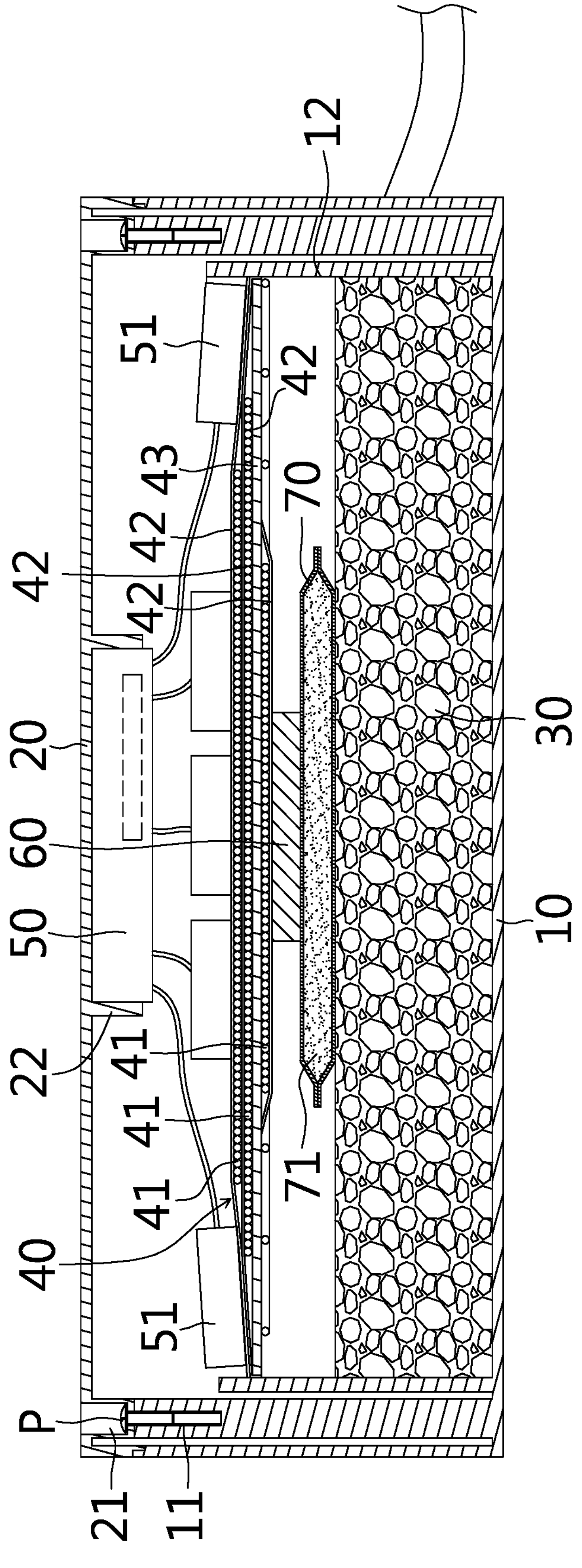
FIG. 2 is a cross sectional view showing the assembly of the quantum graphene generator according to the preferred embodiment of the present invention.
Figure 3:
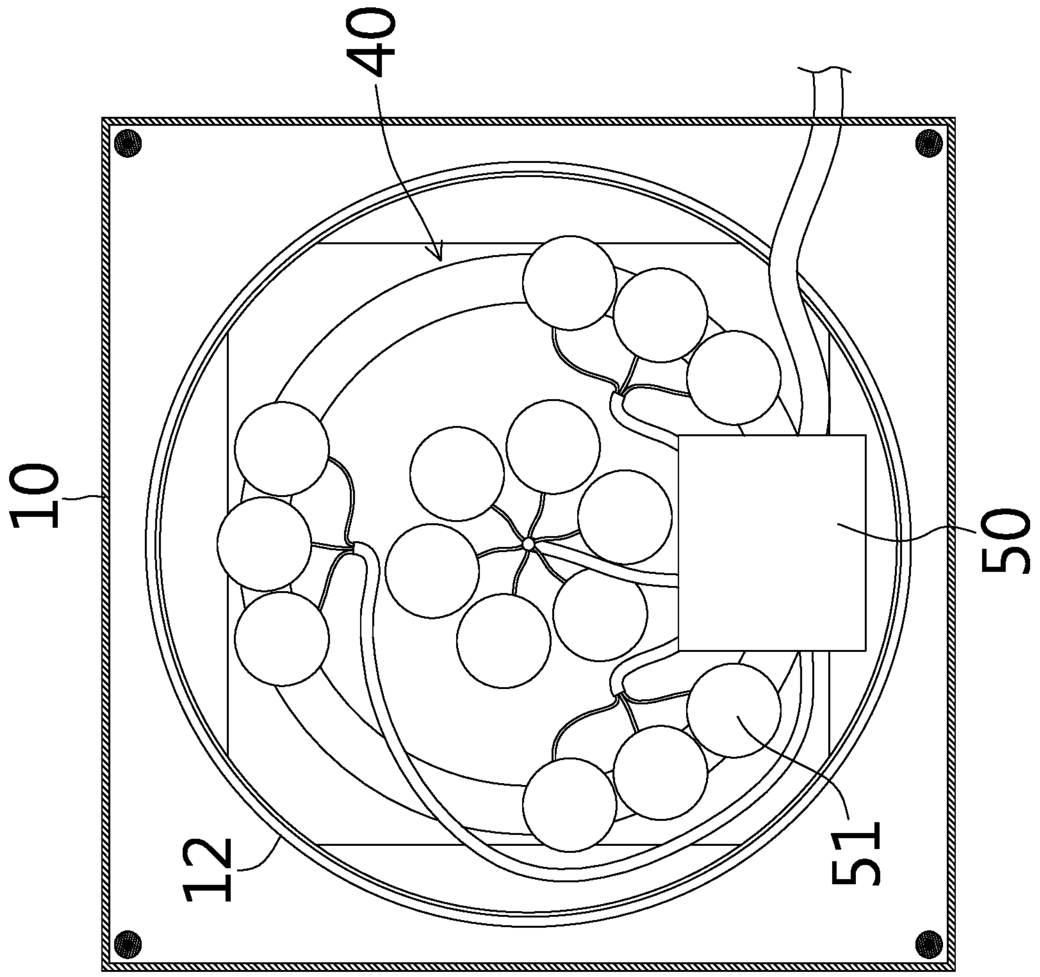
FIG. 3 is a side plan view showing the assembly of the assembly of the quantum graphene generator according to the preferred embodiment of the present invention.

FIG. 1 is a perspective view showing the exploded components of a quantum graphene generator according to a preferred embodiment of the present invention. FIG. 2 is a cross sectional view showing the assembly of the quantum graphene generator according to the preferred embodiment of the present invention. FIG. 3 is a side plan view showing the assembly of the assembly of the quantum graphene generator according to the preferred embodiment of the present invention. The quantum graphene generator comprises a far-infrared quantum implantation device which includes: a body 10, a lid 20, a crystal quartz 30, a plasma sheet 40, an intermediate-frequency current device 50, a magnet assembly 60, and an energy medium 70.

The body 10 includes multiple threaded orifices 11 defined therearound and configured to screw with multiple screws P so that the body 10 is connected with the lid 20 by screwing the multiple threaded orifices 11 with the multiple screws P, an accommodation chamber 12 defined in the body 10 and configured to receive the crystal quartz 30, the plasma sheet 40, the magnet assembly 60, and the energy medium 70.

The lid 20 is covered on the body 10, and the lid 20 includes multiple through orifices 21 defined therearound and corresponding to the multiple threaded orifices 11 of the body 10 so that the multiple threaded orifices P of the lid 20 are screwed with the multiple threaded orifices 11 of the body 10 via the multiple through orifices 21, and the lid 20 further includes a receiving space 22 defined therein and configured to accommodate the intermediate-frequency current device 50.

The crystal quartz 30 is received in the accommodation chamber 12 of the body 10, and the crystal quartz 30 has a piezoelectric effect, wherein when the crystal quartz 30 is acted by an applied alternating electric field to produce a mechanical vibration, and when a frequency of the applied alternating electric field is equal to a fixed frequency of the crystal quartz 30, the mechanical vibration increases greatly, thus causing crystal resonance characteristics. The crystal resonance characteristics are applied for a quartz resonator to replace a resonant circuit of coil and capacitor (LC) or a wave filter, thus obtaining a small size, a compact weight, a high reliability, and a stable frequency. Preferably, the crystal resonance characteristics facilities quartz waves of static pulses. The crystal quartz 30 includes the energy medium 70 arranged on a top thereof.

Figure 4:
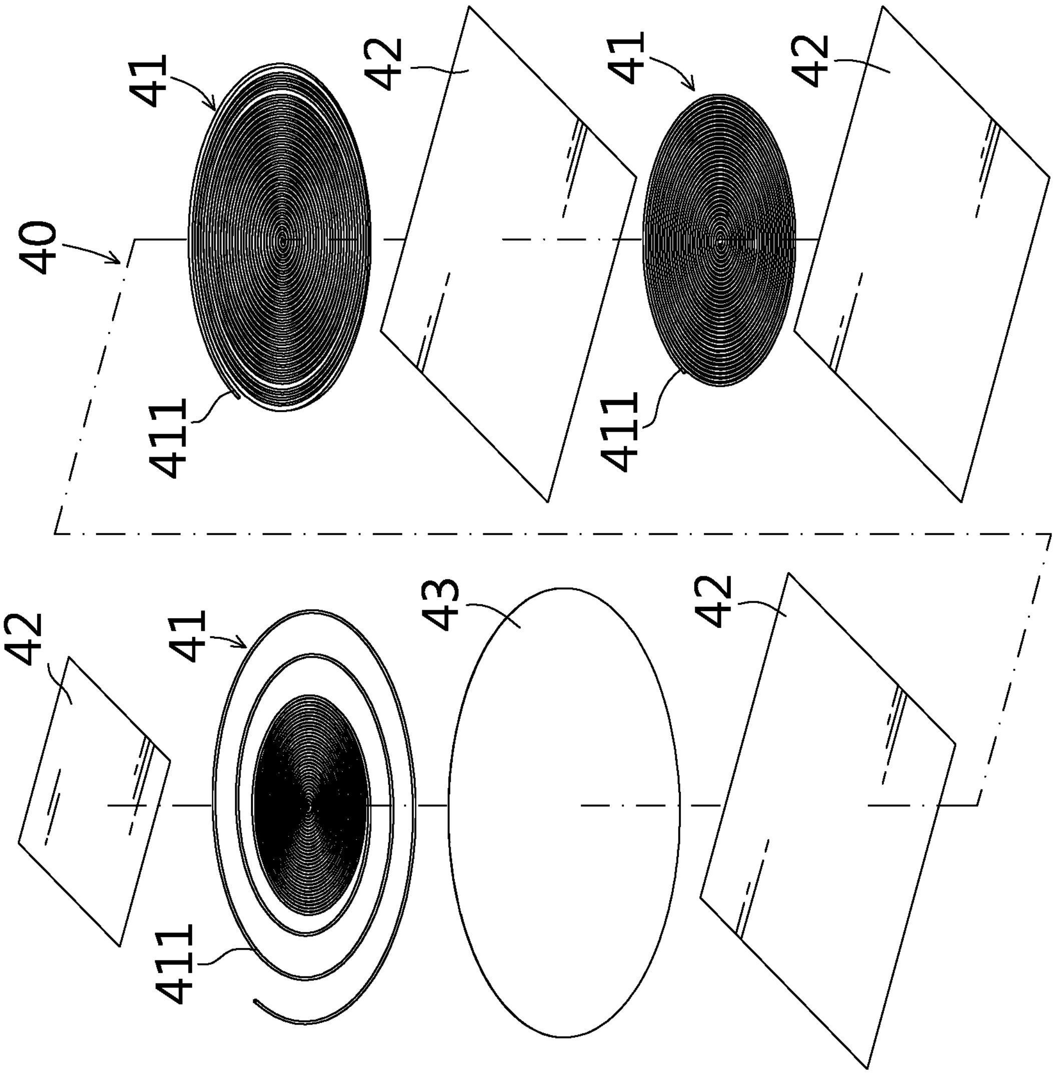
FIG. 4 is a perspective view showing the exploded components of the plasma sheet according to the preferred embodiment of the present invention.
Figure 5:
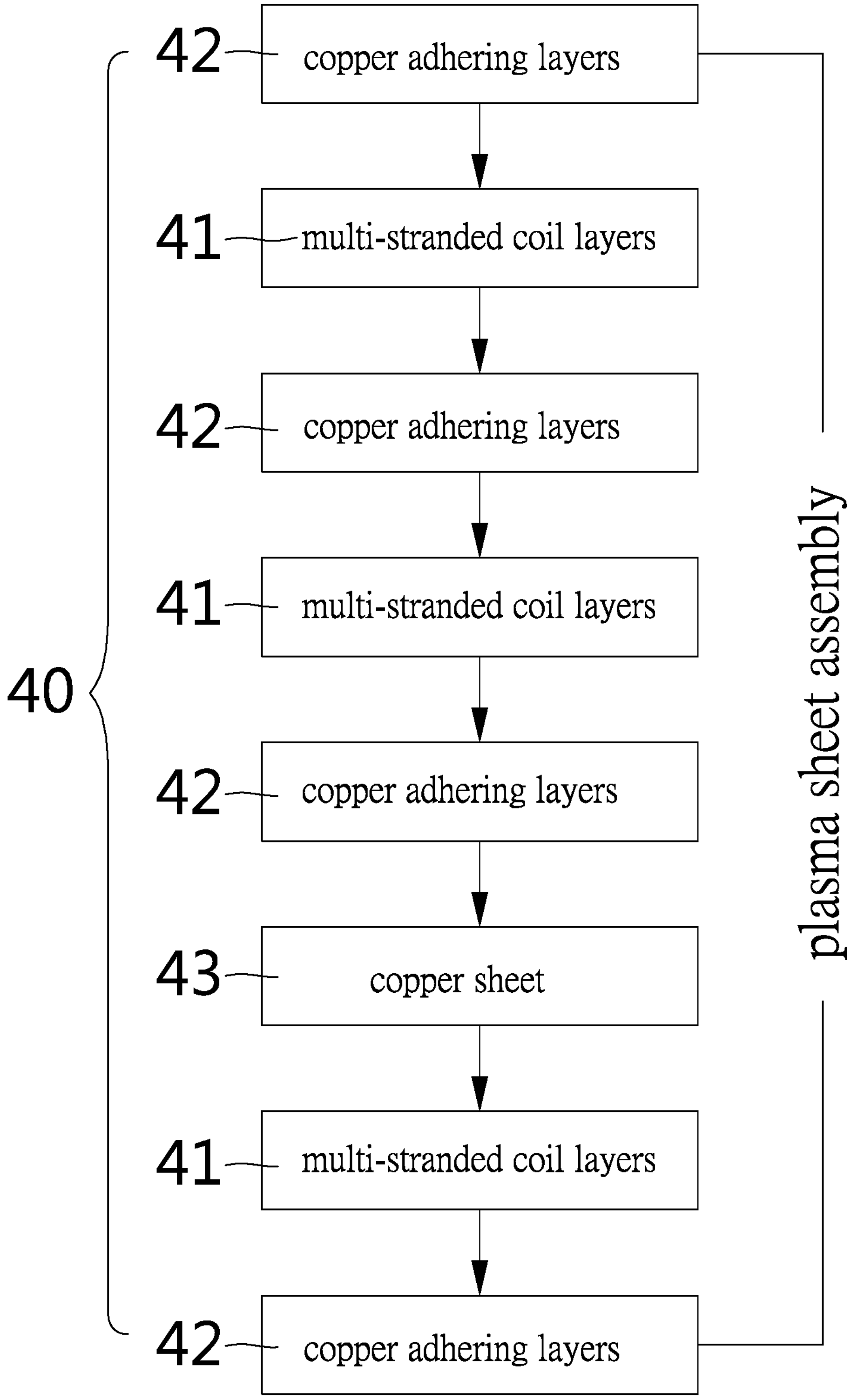
FIG. 5 is a block diagram of a plasma sheet assembly according to the preferred embodiment of the present invention.

FIG. 4 is a perspective view showing the exploded components of the plasma sheet according to the preferred embodiment of the present invention. FIG. 5 is a block diagram of a plasma sheet assembly according to the preferred embodiment of the present invention. The plasma sheet 40 is in a quantum level, wherein the plasma sheet 40 is comprised of three multi-stranded coil layers 41, four copper adhering layers 42, and a copper sheet 43, wherein the three multi-stranded coil layers 41 are made of a copper bundle twisted from multiple copper wires, and the three multi-stranded coil layers 41 are covered by an insulation layer 411, wherein a respective one copper adhering layers 42 is in a plate shape and is stacked with a respective one stranded coil layer 41 and the respective one copper adhering layer 42, wherein the copper sheet 43 is defined between the respective one stranded coil layer 41 and the respective one copper adhering layer 42 to produce radiated waves of a magnetic field.

Figure 6:
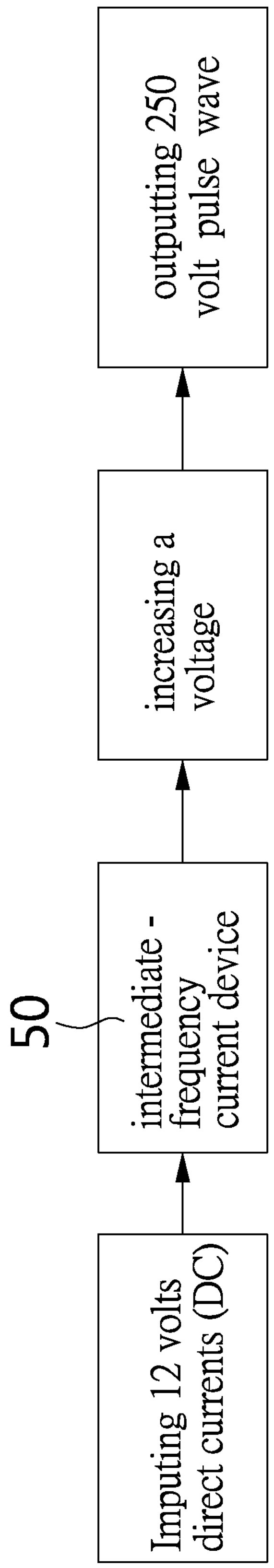
FIG. 6 is a block diagram of the intermediate-frequency current device of the quantum graphene generator according to the preferred embodiment of the present invention.

FIG. 6 is a block diagram of the intermediate-frequency current device of the quantum graphene generator according to the preferred embodiment of the present invention. The intermediate-frequency current device 50 includes multiple magnetic elements 51 (such as NdFeB magnets) which are adhered on a top copper adhering layer 42 of the four copper adhering layers 42 and are configured to increase the radiated waves of the magnetic field, wherein the intermediate-frequency current device 50 inputs 12-volts direct currents (DC) and increases a voltage of the 12-volts direct currents (DC) to output 250 volt pulse wave, thus producing microcurrent.

A top of the magnet assembly 60 is arranged on a middle copper adhering layer 42 below the top copper adhering layer 42, and a bottom of the magnet assembly 60 is located on the energy medium 70 to increase the magnetic field.

The energy medium 70 includes a solid (powered) or liquid graphene 71, wherein the graphene 71 is heated to a predetermined range in a far-infrared quantum implanting process, a top of the energy medium 70 is arranged on a top of the magnet assembly 60, and a bottom of the energy medium 70 is arranged on the top of the crystal quartz, such that far-infrared quantum is implanted to the graphene 71, thus releasing far-infrared quantum from the graphene 71.

Thereby, the far-infrared quantum implantation device is applicable for the quantum graphene generator.

Figure 7:
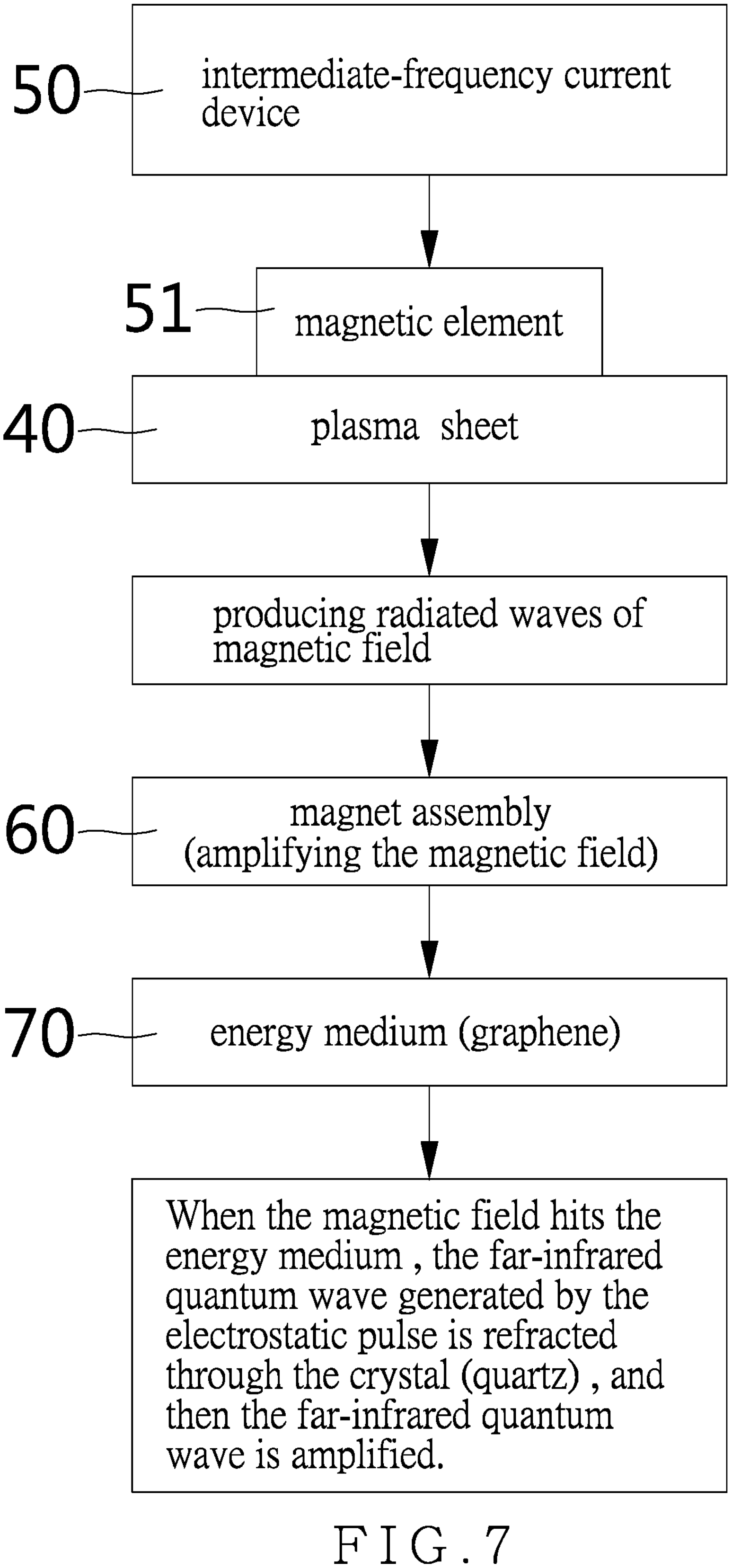
FIG. 7 is a flow chart showing the application of the far-infrared quantum implantation device.

FIG. 7 is a flow chart showing the application of the far-infrared quantum implantation device. When the intermediate-frequency current device 50 outputs the microcurrent, the microcurrent produces the radiated waves of the magnetic field via the multiple magnetic elements 51 and the four copper adhering layers 42, then the magnet assembly 60 increases the magnetic field and the magnetic field impacts the energy medium 70 to produce far-infrared quantum waves of electrostatic pulses via the crystal quartz 30 and to refract and increase the far-infrared quantum waves of the electrostatic pulses. When the magnetic field hits the energy medium, the far-infrared quantum wave generated by the electrostatic pulse is refracted through the crystal (quartz), and then the far-infrared quantum wave is amplified.

Figure 8:
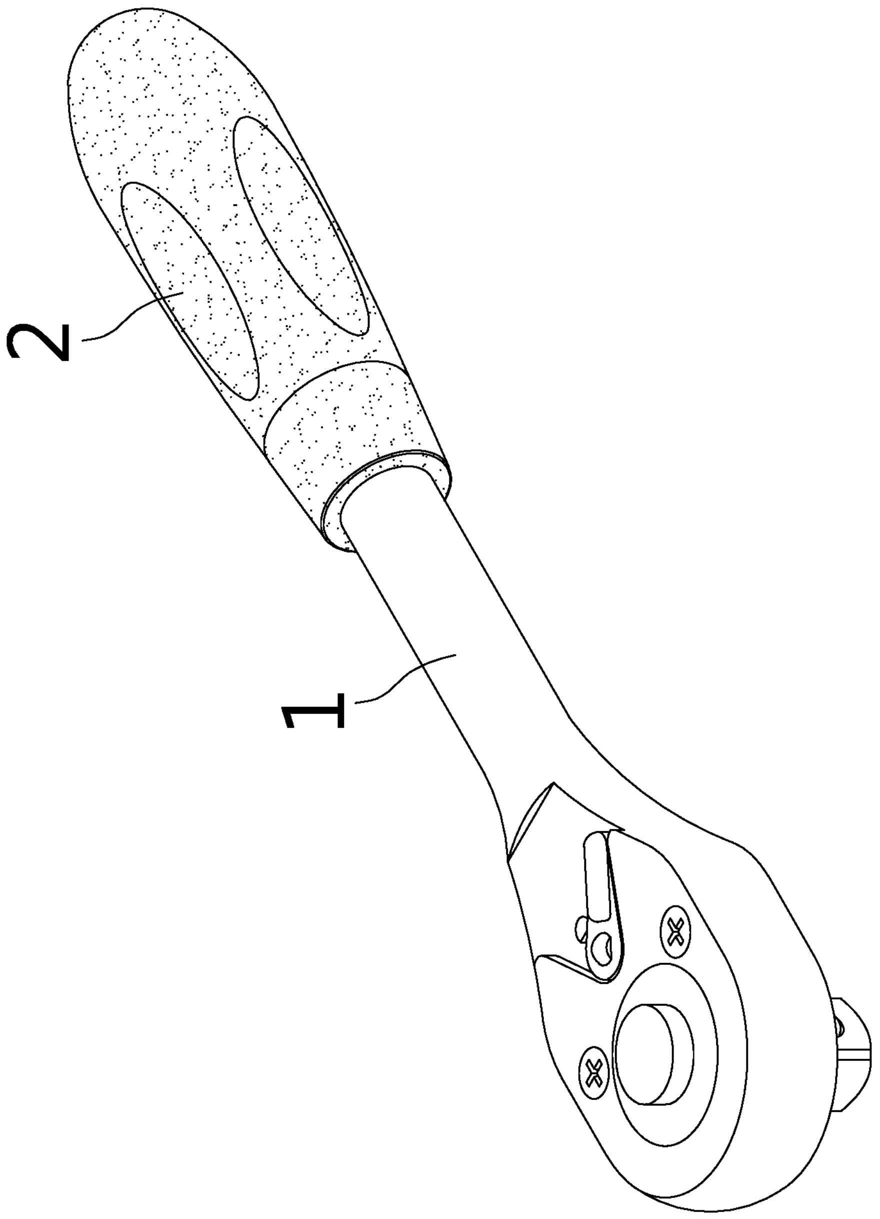
FIG. 8 is a perspective view showing the application of the far-infrared quantum implantation device.

FIG. 8 is a perspective view showing the application of the far-infrared quantum implantation device. For example, a handle 2 of a hand tool 1 is made from the graphene 71 of the energy medium 70.

When introducing elements of the present invention or the preferred embodiments thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A quantum graphene generator comprising: a far-infrared quantum implantation device which includes: a body, a lid, a crystal quartz, a plasma sheet, an intermediate-frequency current device, a magnet assembly, and an energy medium;

wherein the body includes an accommodation chamber defined therein and configured to receive the crystal quartz, the plasma sheet, the magnet assembly, and the energy medium;

wherein the lid is covered on the body, and the lid includes a receiving space defined therein and configured to accommodate the intermediate-frequency current device;

wherein the crystal quartz is received in the accommodation chamber of the body, and the crystal quartz includes the energy medium arranged on a top thereof;

wherein the plasma sheet is a plasma sheet assembly which is in a quantum level, the plasma sheet is comprised of multiple multi-stranded coil layers, multiple copper adhering layers, and a copper sheet, wherein the multiple multi-stranded coil layers are made of a copper bundle twisted from multiple copper wires, and the multiple multi-stranded coil layers are covered by an insulation layer, wherein a respective one copper adhering layers is in a plate shape and is stacked with a respective one stranded coil layer and the respective one copper adhering layer, and the copper sheet is defined between the respective one stranded coil layer and the respective one copper adhering layer to produce radiated waves of a magnetic field;

wherein the intermediate-frequency current device includes multiple magnetic elements which are adhered on a top copper adhering layer of the multiple copper adhering layers and are configured to increase the radiated waves of the magnetic field, and the intermediate-frequency current device inputs direct currents (DC) and increases a voltage of the DC to produce high-voltage microcurrent, the microcurrent produces the radiated waves of the magnetic field via the multiple magnetic elements and the multiple copper adhering layers, then the radiated waves of the magnetic field impact the crystal quartz to generate electric pulse wave;

wherein a top of the magnet assembly is arranged on a middle copper adhering layer below the top copper adhering layer, and a bottom of the magnet assembly is located on the energy medium to increase the magnetic field; and wherein the energy medium includes a graphene defined therein, a top of the energy medium is arranged on the magnet assembly, and a bottom of the energy medium is arranged on the top of the crystal quartz, such that far-infrared quantum is implanted to the graphene, thus releasing far-infrared quantum from the graphene.

2. The quantum graphene generator as claimed in claim 1, wherein the graphene energy medium is heated to a predetermined range in a far-infrared quantum implanting process.

3. The quantum graphene generator as claimed in claim 1, wherein the graphene is solid and powered.

4. The quantum graphene generator as claimed in claim 1, wherein the graphene is a liquid.

5. The quantum graphene generator as claimed in claim 4, wherein a handle of a hand tool is made from the graphene of the energy medium.

* * * * *